US00PP19619P2

(12) United States Plant Patent
Zaiger et al.

(10) Patent No.: US PP19,619 P2
(45) Date of Patent: Jan. 6, 2009

(54) INTERSPECIFIC PRUNUS TREE NAMED 'RUBY KAT'

(50) Latin Name: *Prunus species*
Varietal Denomination: Ruby Kat

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/012,467

(22) Filed: Feb. 4, 2008

(51) Int. Cl.
*A01H 5/00* (2006.01)

(52) U.S. Cl. ..... Plt./180

(58) Field of Classification Search ..... Plt./180
See application file for complete search history.

*Primary Examiner*—Annette H Para

(57) ABSTRACT

A new and distinct variety of interspecific tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous upright growth.
2. Heavy and regular production of fruit.
3. Fruit with red flesh having very good flavor and eating quality.
4. Fruit having a good balance between acid and sugar with an average Brix of 18.6°.
5. Fruit with an attractive red skin color.

1 Drawing Sheet

Botanical description: *Prunus species.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum and interspecific trees, which are known to us, and mentioned herein, 'Emerald Beaut' Plum (U.S. Plant Pat. #9,162), and 'Flavor Jewel' Interspecific (U.S. Plant Pat. #13,502).

ORIGIN OF THE VARIETY

The present new variety of interspecific tree [(*Prunus salicina*)×(*Prunus salicina*×*Prunus armeniaca*)×*Prunus salicina*] was originated by us in our experimental orchard located near Modesto, Calif. as a first generation seedling from a cross between 'Flavor Jewel' Interspecific (U.S. Plant Pat. #13,502) (the seed parent) and 'Emerald Beaut' Plum (U.S. Plant Pat. #9,162) (pollen parent). A large number of these first generation seedlings were grown and budded by us to established trees of 'Nemaguard' Rootstock (non-patented) to enhance early production of fruit. Under close and careful observation, one seedling which is the present variety exhibited desirable tree and fruit characteristics and was selected in 2004 for additional asexual propagation and commercialization.

ASEXUAL REPRODUCTION OF THE VARIETY

Additional asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [(Plum× Plumcot)×Plum)], is of large size, vigorous, upright growth and a productive and regular bearer of large size, red flesh fruit with very good flavor and eating quality. The fruit is further characterized by being nearly globose in shape, having an attractive dark red skin color with firm flesh, holding firm on the tree 7 to 10 days after maturity, having a good balance between acid and sugar with an average Brix of 18.6°. In comparison to its seed parent 'Flavor Jewel' Interspecific (U.S. Plant Pat. #13,502), the fruit of the new variety is larger in size, has red flesh compared to yellow flesh and is approximately 25 days earlier in maturity. In comparison to the fruit of the pollen parent 'Emerald Beaut' Plum (U.S. Plant Pat. #9,162), the fruit of the new variety is larger in size, has red skin compared to green, red flesh compared to whitish yellow and approximately 10 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large. Pruned to 3 to 3.5 meters in height for economical harvesting of fruit. Average width 3 meters, varies with different cultural practices and climatic conditions.

*Vigor.*—Vigorous, tree growth of approximately 1.5 to 2 meters in height the first growing season.

*Form.*—Upright, usually pruned to vase shape.

*Branching habit.*—Upright, crotch angle approximately 35°, increase with heavy crop load.

*Productivity.*—Productive, thinning and spacing of fruit necessary for desired market size fruit.

*Bearer.*—Regular, adequate fruit set 4 consecutive years. No alternate bearing observed.

*Fertility.*—Self sterile, pollinator required.

*Density.*—Medium dense, usually pruned to vase shape to allow sunlight to center of tree to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

Trunk:

*Size.*—Medium to large. Average circumference 39.4 cm, measured at 25.4 cm above ground level on a 5 year old tree.

*Stocky.*—Medium.

*Texture.*—Medium shaggy, increases with age of tree.

*Color.*—Varies from 7.5YR 2/2 to 10YR 4/2.

Branches:

*Size.*—Medium. Average circumference 13.9 cm at 1 meter above ground.

*Surface texture.*—New growth relatively smooth. Mature growth medium rough, roughness increases with age.

*Lenticels.*—Average number 41 in a 25.8 square cm surface of branch. Average length 3.6 mm. Average width 1.6 mm. Color varies from 7.5YR 5/8 to 7.5YR 5/10.

*Color.*—New growth varies from 2.5GY 7/6 to 7.5RY 7/2. Mature growth varies from 5YR 3/4 to 7.5YR 6/2, varies with age of growth.

Leaves:

*Size.*—Medium. Average length 107.4 mm. Average width 48.6 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Size — medium. Average length 13.4 mm. Average width 1.3 mm. Color varies from 2.5GY 6/6 to 2.5GY 6/8. Longitudinally grooved. Surface — pubescent, very short in length.

*Glands.*—Type — globose. Size — small. Average length 0.7 mm. Average diameter 0.3 mm. Number — average 3, varies from 2 to 4. Location — primarily on base of leaf blade and upper portion of petiole. Color varies from 2.5GY 5/6 to 5GY 5/6.

*Color.*—Upper surface varies from 5GY 3/4 to 5GY 3/6. Lower surface varies from 5GY 4/4 to 5GY 4/6. Midvein color varies from 2.5GY 8/6 to 2.5GY 7/6.

Flower buds:

*Size.*—Small to medium. Average length 8.2 mm. Average diameter 4.7 mm.

*Hardiness.*—Hardy with respect to California winters.

*Form.*—Conical, becoming slightly elongated before opening.

*Pedicel.*—Average length 8.3 mm. Average width 0.6 mm. Color varies from 5GY 7/8 to 5GY 6/8. Surface — glabrous.

*Color*—N 9.5/ (white).

*Number of buds per spur.*—Average 5, varies from 2 to 7.

Flowers:

*Blooming period.*—Date of First Bloom Mar. 1, 2007. Date of Petal Fall Mar. 11, 2007, varies slightly with climatic conditions.

*Size.*—Small to medium. Average height 11.2 mm. Average diameter 14.2 mm.

*Petals.*—Number — 5, alternately arranged to sepals. Size — small to medium. Average length 9.8 mm. Average width 7.7 mm. Form — orbicular, narrows at point of attachment. Margin — sinuate. Surface — upper and lower both surfaces glabrous. Color — N 9.5/ (white).

*Sepals.*—Number — 5, alternately arranged to petals. Size — small. Average length 3.3 mm. Average width 2.5 mm. Shape — triangular, apex rounded. Surface — both upper and lower surfaces glabrous. Margin — entire. Color — upper surface varies from 5GY 6/6 to 5GY 6/8. Lower surface varies from 2.5GY 6/8 to 5GY 6/8.

*Stamens.*—Average number per flower 29. Average filament length 7.8 mm. Filament color N 9.5/ (white). Anther color varies from 5Y 8/8 to 7.5Y 8/10.

*Pollen.*—Self sterile, pollinator required. Color varies from 5Y 7/8 to 5Y 7/10.

*Pistil.*—Normally one, varies from 1 to 2. Surface — glabrous. Average length 7.8 mm. Position of stigma average of 0.7 mm below anthers. Color varies from 2.5GY 8/6 to 2.5GY 7/6.

*Fragrance.*—Moderate.

*Color.* —N 9.5/ (white).

*Number flowers per flower bud.*—Average 2, varies from 1 to 3.

*Pedicel.*—Average length 9.3 mm. Average width 0.5 mm. Color varies from 2.5GY 6/8 to 2.5GY 6/10. Surface — glabrous.

Fruit:

*Maturity when described.*—Firm ripe.

*Date of first picking.*—Jul. 15, 2007.

*Date of last picking.*—Jul. 24, 2007, varies slightly with climatic conditions.

*Size.*—Large. Average diameter axially 65.4 mm. Average transversely in suture plane 66.9 mm. Average weight 204.5 grams, varies slightly with fertility of the soil, amount of thinning and climatic conditions.

*Form.*—Nearly globose, slightly enlarged near apex.

*Suture.*—Shallow, extends from base to apex.

*Ventral surface.*—Nearly smooth on majority of the fruit.

*Apex.*—Rounded to small apical protrusion.

*Base.*—Rounded to slightly retuse.

*Cavity.*—Rounded to slightly elongated in suture plane. Average depth 6.1 mm. Average diameter 7.6 mm.

Stem:

*Size.*—Small. Average length 14.0 mm. Average diameter 2.6 mm.

*Color.*—Varies from 10Y 7/6 to 5YR 3/6.

Flesh:

*Ripens.*—Evenly.

*Texture.*—Firm, meaty.

*Fibers.*—Few, small, tender.

*Firmness.*—Good, comparable to the commercial interspecific 'Flavor Jewel' (U.S. Plant Pat. #13,502).

*Aroma.*—Moderate.

*Amydgalin.*—Undetected.

*Eating quality.*—Very good.

*Flavor.*—Very good, good balance between acid and sugar.

*Juice.*—Moderate, enhances flavor.

*Brix.*—Average of 18.6° Brix, varies slightly with amount of fruit per tree and climatic conditions.

*Color.*—Varies from 5R 4/10 to 7.5R 3/12. Pit cavity varies from 10R 3/6 to 2.5YR 4/6.

Skin:

*Thickness.*—Medium.

*Surface.*—Varies from smooth to slightly waffled.

*Bloom.*—Moderate amount, completely covered.

*Tendency to crack.*—Very slight.

*Color.*—Ground color varies from 5Y 9/4 to 5Y 8/4. Overspread with 2.5R 2/4 to 5R 3/6.

*Tenacity.*—Tenacious to flesh.

*Astringency.*—Undected.

Stone:

*Type.*—Clingstone.

*Size.*—Large. Average length 27.4 mm. Average width 19.9 mm. Average thickness 13.5 mm.

*Form.*—Ovoid.

*Base.*—Varies from flat to slightly rounded.

*Apex.*—Slightly pointed. Average length 0.4 mm.

*Surface.*—Slightly pitted throughout, one short groove on each side of suture extending from base toward apex.

*Sides.*—Unequal, one side extending slightly further from suture plane.

*Ridges.*—One short small ridge on each side of suture extending from base toward apex.

*Tendency to split.*—None.

*Color.*—Varies from 5YR 5/8 to 5YR 4/6.

Kernel:

*Size.*—Medium. Average length 17.3 mm. Average width 11.3 mm. Average depth 6.8 mm.

*Shape.*—Ovate.

*Viability.*—Viable, complete embryo development.

*Skin.*—Color varies from 5Y 9/4 to 7.5Y 9/4.

Use: Dessert. Market — local and long distance.

Keeping quality: Good, held firm in cold storage for 21 days at 38 to 42° F. without internal breakdown of flesh or appreciable loss of flavor.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claim:

1. A new and distinct variety of interspecific tree, substantially as illustrated and described, characterized by its large size, vigorous, upright growth with heavy production and a regular bearer of large, firm, red flesh fruit with very good flavor and eating quality; the fruit is further characterized by having an attractive red skin and flesh color, with good storage and shipping quality.

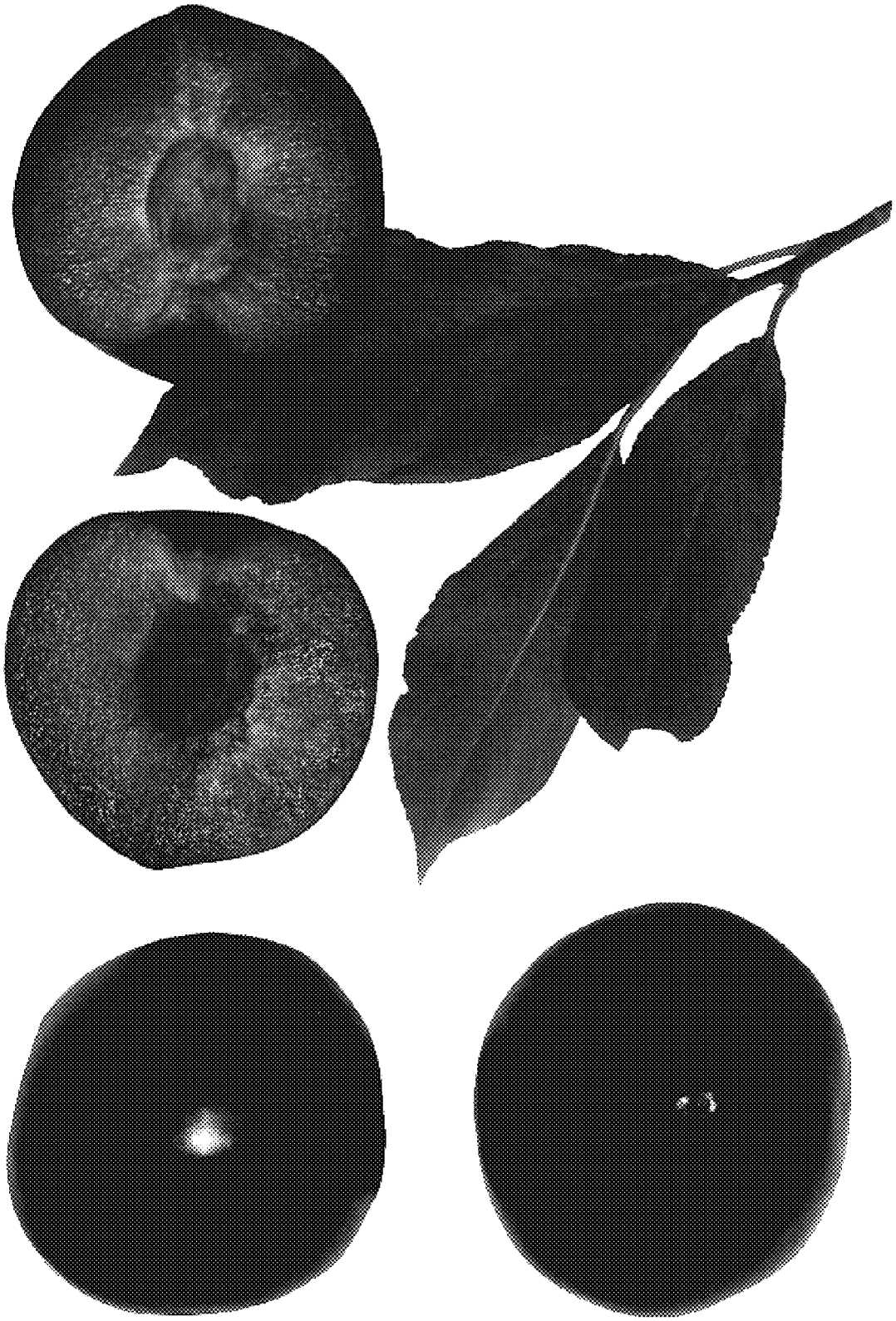

* * * * *